(12) United States Patent
Walters et al.

(10) Patent No.: US 7,038,445 B2
(45) Date of Patent: May 2, 2006

(54) METHOD, SYSTEM AND APPARATUS FOR FERROMAGNETIC WALL MONITORING

(75) Inventors: William T. Walters, LaMarque, TX (US); Danny J. Uselton, The Woodlands, TX (US); Robert W. Speiser, Pasadena, TX (US)

(73) Assignee: Scan Systems, Corp., The Woodlands, TX (US)

( * ) Notice: Subject to any disclaimer, the term of this patent is extended or adjusted under 35 U.S.C. 154(b) by 276 days.

(21) Appl. No.: 10/229,696

(22) Filed: Aug. 28, 2002

(65) Prior Publication Data

US 2004/0041560 A1    Mar. 4, 2004

(51) Int. Cl.
*G01N 27/82* (2006.01)

(52) U.S. Cl. .................................................... 324/240

(58) Field of Classification Search ................ 324/238, 324/206, 216, 217, 225, 235, 227, 207.24, 324/228, 234, 239, 240, 242, 243; 702/38
See application file for complete search history.

(56) References Cited

U.S. PATENT DOCUMENTS

| | | | |
|---|---|---|---|
| 2,467,306 A * | 4/1949 | Habig ........................ 324/242 |
| 3,611,121 A * | 10/1971 | Vild et al. .................. 324/238 |
| 3,843,923 A * | 10/1974 | deVries et al. ............. 324/228 |
| 4,510,447 A | 4/1985 | Moyer | |
| 4,629,991 A * | 12/1986 | Wheeler ...................... 324/332 |
| 4,704,580 A * | 11/1987 | Moake et al. ................ 324/242 |
| 4,710,712 A * | 12/1987 | Bradfield et al. ........... 324/227 |
| 5,137,677 A * | 8/1992 | Murata ................... 264/272.16 |
| 5,245,279 A | 9/1993 | Bendzsak | |
| 5,532,591 A | 7/1996 | Logue | |
| 5,537,035 A | 7/1996 | Fowler et al. | |
| 5,537,038 A | 7/1996 | Ando | |
| 5,581,037 A | 12/1996 | Kwun et al. | |
| 5,670,578 A | 9/1997 | Shawl | |
| 5,671,155 A * | 9/1997 | Edens et al. .................. 702/38 |
| 5,675,251 A | 10/1997 | MacLean et al. | |
| 5,747,998 A | 5/1998 | Fowler et al. | |
| 5,751,144 A | 5/1998 | Weischedel | |
| 5,914,596 A * | 6/1999 | Weinbaum .................. 324/228 |
| 5,943,632 A * | 8/1999 | Edens et al. .................. 702/38 |
| 6,014,024 A | 1/2000 | Hockey et al. | |
| 6,014,091 A * | 1/2000 | Noltemeyer et al. ........... 341/7 |
| 6,057,684 A | 5/2000 | Murakami et al. | |
| 6,087,830 A | 7/2000 | Brandly et al. | |
| 6,150,809 A | 11/2000 | Tiernan et al. | |
| 6,172,501 B1 | 1/2001 | Tsukada et al. | |
| 6,316,937 B1 * | 11/2001 | Edens ........................ 324/220 |
| 6,356,072 B1 * | 3/2002 | Chass ....................... 324/207.2 |
| 6,498,451 B1 * | 12/2002 | Boules et al. ................ 318/661 |
| 2003/0112006 A1 * | 6/2003 | Luetzow ................. 324/207.21 |

* cited by examiner

*Primary Examiner*—Bot Ledynh
*Assistant Examiner*—Kenneth J. Whittington
(74) *Attorney, Agent, or Firm*—Jeffrey L. Wendt (57) ABSTRACT

A device and method is taught for detection of flaws and localized wall loss in pipes made of ferromagnetic-based material. The device utilizes a magnetic field generator to create a horizontal magnetic field of flux. A pipe is passed through the magnetic field where a magnetic fluctuation detector, for example multiple groups of hall units, identifies fluctuations in the magnetic field.

31 Claims, 6 Drawing Sheets

Output=$H_1+H_2+H_3+H_4$

METHOD, SYSTEM AND APPARATUS FOR FERROMAGNETIC WALL MONITORING

BACKGROUND OF THE INVENTION

1. Field of the Invention

The field of this invention relates generally to a method, system and apparatus for ferromagnetic wall monitoring, and more particularly to a method, system and apparatus for detecting flaws in pipe.

2. General Background of the Invention

Corrosion and wear commonly occurs in well pipe used in oil and gas production operations.

Various devices are known for detecting flaws in the walls of ferromagnetic pipe. For example, U.S. Pat. No. 4,510,447 (Moyer) discloses an apparatus that comprises an electromagnetic having poles in slideable contact with the surface of the wall of ferromagnetic pipe to form a closed magnetic circuit and means for electrically connecting the coil of the electromagnetic to an input source of alternating current whereby a fluctuating magnetic field is induced generally axially through the wall of the pipe between the poles of the electromagnetic.

U.S. Pat. No. 5,245,279 (Bendzsak) discloses a direct-current electromagnetic device for nondestructively detecting localized discontinuities in ferromagnetic objects. The device comprises an adjustable dc exciter means, a magnetic flux injector means, an external magnetic field detector means, a plurality of position sensors, a signal processing means and a control means.

U.S. Pat. No. 5,532,591 (Logue) discloses an apparatus for detecting surface flaws in cylindrical articles by means of asymmetric magnetic detection, utilizing a rotating magnetic field, said articles having central longitudinal axes, apparatus having a guide assembly for guiding the cylindrical articles along a displacement path having a central longitudinal axis extending coaxially of the central longitudinal axes of the articles and a pair of multiple polar sensor assemblies positioned in annular relationship with the displacement path for producing a plurality of phase/amplitude modulated signals representative of the surface geometry of the inspected cylindrical article, also disclosed are two embodiments of cylindrical container flange imperfection detector apparatus utilizing multiple polar sensor assemblies.

U.S. Pat. No. 5,537,035 (Fowler, et al.) discloses an apparatus and method for detecting anomalies in ferrous pipe structures. A sensor having one or more sensor shoe members is placed in the interior of a ferrous pipe structure to be inspected. Each sensor shoe member has one or more magnetic field generating apparatus, with a three-axis flux-gate magnetometer for detecting magnetic fields in the region of the ferrous pipe structure adjacent to which the sensor shoe member is placed. Any magnetic fields in the pipe structure, whether imposed externally, or remnant, which are detected, are sensed and resolved into components in three mutually orthogonal directions for enhanced accuracy.

U.S. Pat. No. 5,675,251 (MacLean, et al) and U.S. Pat. No. 6,087,830 (Brandly, et al.) disclose a device for inspecting the integrity of water distribution pipelines. The device is constructed of housing units, for housing inspection circuitry. The housing units are connected by flexible connectors which permit the units to move out of axial alignment to pass bends. The device is able to negotiate bends and pass through openings of reduced size in the pipeline. The device can be used with various inspection technologies including remote field eddy current inspection technology.

U.S. Pat. No. 6,104,024 (Hockey, et al.) discloses a magnet and sensor coil unilaterial and in relative motion to a conductive material, to measure perturbation or variation in the magnetic field in the presence of a flaw. A liftoff compensator measures a distance between the conductive material and the magnet.

U.S. Pat. No. 6,172,501 (Tsukada, et al.) discloses a detecting coil device mounted on part of a cable to evaluate the degree of corrosion of the cable, which is used, for example, on suspension or skew bridges. The detecting coil device is provided with a detecting coil and Hall elements. A magnetizer having a magnetizing coil is mounted as to enclose the cable and the detecting coil device. When current flows through the magnetizing coil, the current magnetizes the cable. The magnetic field strength is detected by the Hall element, and the amount of magnetic flux passing through the cable is detected using the detecting coil.

The foregoing references are incorporated herein setting forth part of the state of the art of the present invention.

SUMMARY AND DESCRIPTION OF THE INVENTION

In one aspect of the invention a ferromagnetic wall monitoring device comprises a magnetic field generator having an inner and outer circumference. A plurality of groups of magnetic fluctuation detectors are mounted about the magnetic field generator. Preferably the magnetic field generator is an encircling coil. The magnetic fluctuation detectors may be affixed to the magnetic field generator or may be mounted in a separate housing apart from the magnetic field generator. A summing circuit interconnects the plurality of groups of magnetic fluctuation detectors for adding together the voltage output of each of the groups of magnetic fluctuation detectors.

In a specific embodiment, the magnetic filed generator is a circular coil having multi-turns of wire located in the coil.

In another embodiment, the wall monitoring device additionally comprises a group or groups of magnetic fluctuation detectors mounted about the outer circumference of the magnetic field generator.

In a preferred embodiment the groups of magnetic fluctuation detectors are mounted substantially equidistant from one another. The preferred magnetic fluctuation detector is a hall unit, however, other such devices may be utilized, for example, magneto resistors and magneto diodes. They may also be utilized in combination.

In one aspect of the invention a method for ferromagnetic wall monitoring comprises the steps of (a) providing a plurality of magnetic field fluctuation detectors mounted about the inner circumference of a magnetic field generator, (b) generating a magnetic field with said magnetic field generator, (c) passing a ferromagnetic object through said magnetic field, and (d) determining flaws in the ferromagnetic objects by identifying magnetic field fluctuations with the plurality of magnetic field fluctuation detector. The metallic object is preferably a pipe as defined herein.

In a preferred embodiment the groups of magnetic fluctuation detectors are mounted substantially equidistant from one another. The preferred magnetic fluctuation detectors are selected from hall units, magneto resistors, magneto diodes and combinations thereof.

In a preferred embodiment, the magnetic field fluctuation detectors are hall units. Other similar devices may be utilized with the method, such as magneto resistors and magneto diodes. They may also may be utilized in combination.

A further aspect of the method is determining a sum of all voltage from each of the hall units and detecting a change of voltage in said hall units when passing a portion of pipe with a flaw past the hall units. Monitoring a signal generated by the hall units when the metallic object passes near the hall units, then includes recording or capturing the signal. A filter can be used to clean the signal received from the hall units. The signal can be displayed electronically via a computer printed to a printing or plotting device.

In a preferred embodiment, the magnetic field fluctuation detectors are hall units. Other similar devices may be utilized with the method, selected from magneto resistors, magneto diodes, and combinations of hail units, magneto resistors, and magneto diodes.

The number of flux lines flowing through the hall sensor will be a function of the wall thickness of the material being monitored. Therefore, this monitoring device of the hall units spaced within the inside circumference of a magnetic coil provides the means of measuring the wall thickness of the pipe.

In one aspect of the invention, an ore circuit is interconnected with each group of magnetic fluctuation detectors so that the largest signal generated from a group of hall units may be determined.

In another aspect of the invention, a defect monitor is interconnected with each group of the magnetic fluctuation detectors to identify defective hall units.

The term "pipe," as used herein, includes any pipe, hose, tube, pole, shaft, cylinder, duct, rod, oil field tubular, tubing for the flow of oil or gas, casing, drill pipe, oil field tubulars and equivalents thereof made in whole or part of a ferromagnetic material.

The term "flaws," used herein, includes any defects, discontinuities or irregularities in the walls of the pipe, for example, seams, cracks, chips, and unusual wear.

The term "magnetic field fluctuation detector," used herein, includes hall units, magneto diodes and magneto resistors. Preferably the magnetic fluctuation detector utilized with the invention is a hall unit.

The term "hall unit," as used herein, includes any Hall sensor, and any device or sensor which produces a voltage in relation to a magnetic field applied to the sensor. Although well known, a brief description of the hall sensor is provided. A Hall sensor is generally manufactured as a four terminal solid state device which produces an output voltage proportional to the product of an input current, a magnetic flux density and the sine of the angle between magnetic flux density and the plane of the hall sensor. A Hall sensor typically has an active element and two pairs of ohmic contacts. An electric current flows between two contacts aligned in one direction x. This current, the magnitude and direction of which are known from a calibration stage, in the presence of a perpendicular magnetic field, generates a respective Hall voltage in the other two contacts aligned in a transverse direction y. As known, a Hall sensor is sensitive to that component of the magnetic field which is perpendicular to its surface. More specifically, the Hall voltage is responsive to the current flow and to the strength of a magnetic field provided within the vicinity of the Hall sensor.

The term "magnetic field generator," as used herein, includes any device capable of generating a horizontal magnetic field of flux. Preferably the magnetic field generator is a coil such an encircling coil or circular coil with multi-turns of wire located in the cavities of the coil.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

A better understanding of the invention can be obtained from the detailed description of exemplary embodiments set forth below, when considered in conjunction with the appended drawings, in which.

DETAILED DESCRIPTION

It is readily apparent to one skilled in the art that various embodiments and modifications can be made to the invention disclosed in this Application without departing from the scope and spirit of the invention.

Figure 1A:
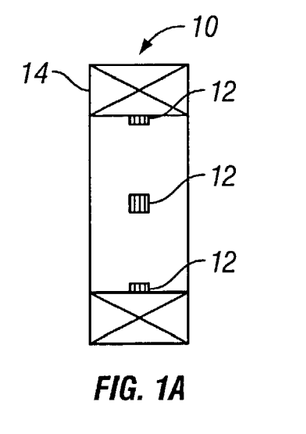
FIG. 1A schematically illustrates a partial, schematic side-view of an embodiment of the present invention.
Figure 1B:
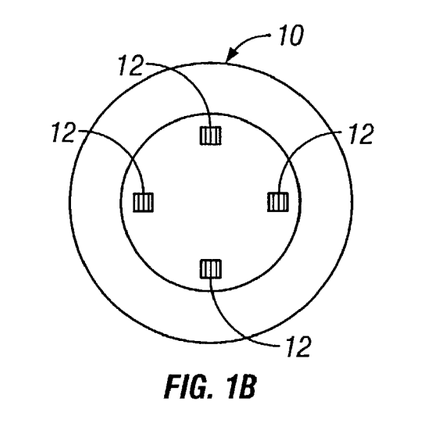
FIG. 1B schematically illustrates an end-view of the embodiment of FIG. 1A.

Referring to FIG. 1A, a partial, sectional side-view of one embodiment of the present invention is illustrated. A magnetic field generator 10 has four hail units 12 positioned substantially equidistant from one another. The magnetic field generator 10 as shown is a coil having a wiring cavity for generating a magnetic field. In FIG. 1B, an end view of the coil illustrated in FIG. 1A is shown. In this embodiment, four hall units are located along the inside circumference of the magnetic field generator. The magnetic field generator 10 has a body portion 14.

Figure 2:
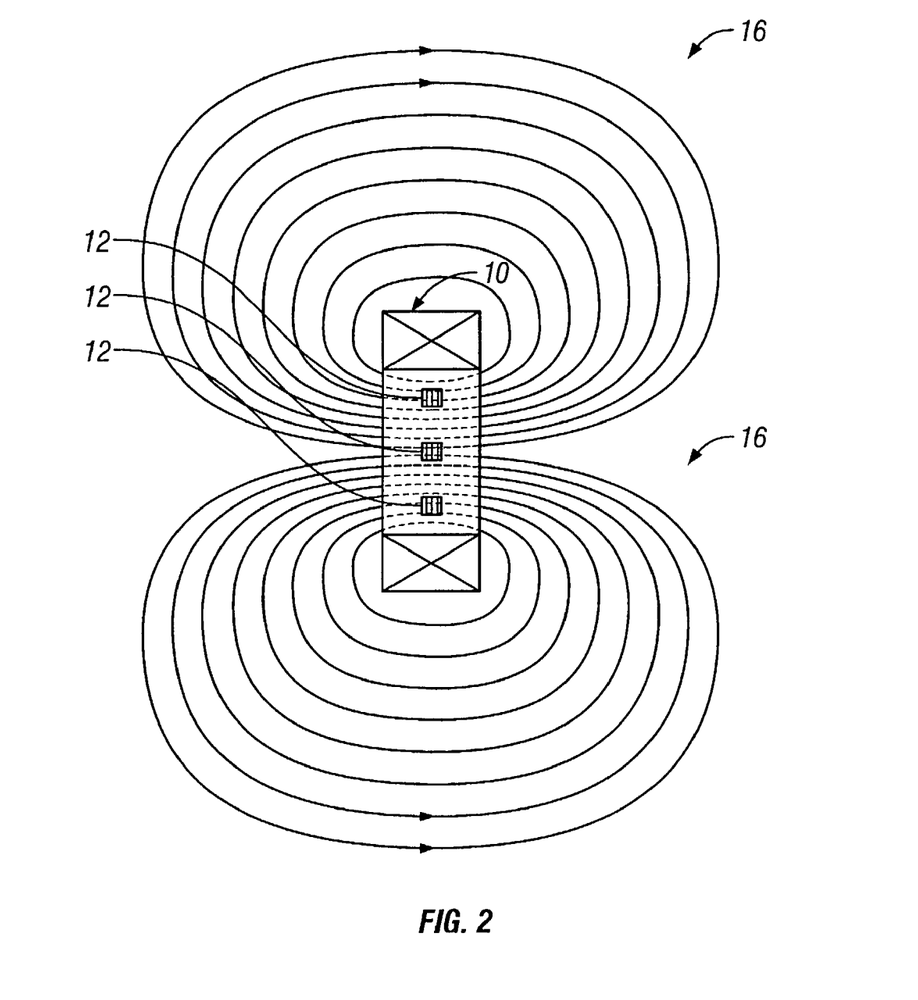
FIG. 2 schematically illustrates a side-view of the embodiment of FIGS. 1A and 1B shown with a magnetic field.

As shown in FIG. 2, exciting the magnetic field generator 10 with a DC current generates magnetic lines of flux 16 that encircle the magnetic field generator 10. Many of these magnetic lines of flux 16 pass through the hall units 12 causing the hall units 12 to generate a voltage.

Figure 3:
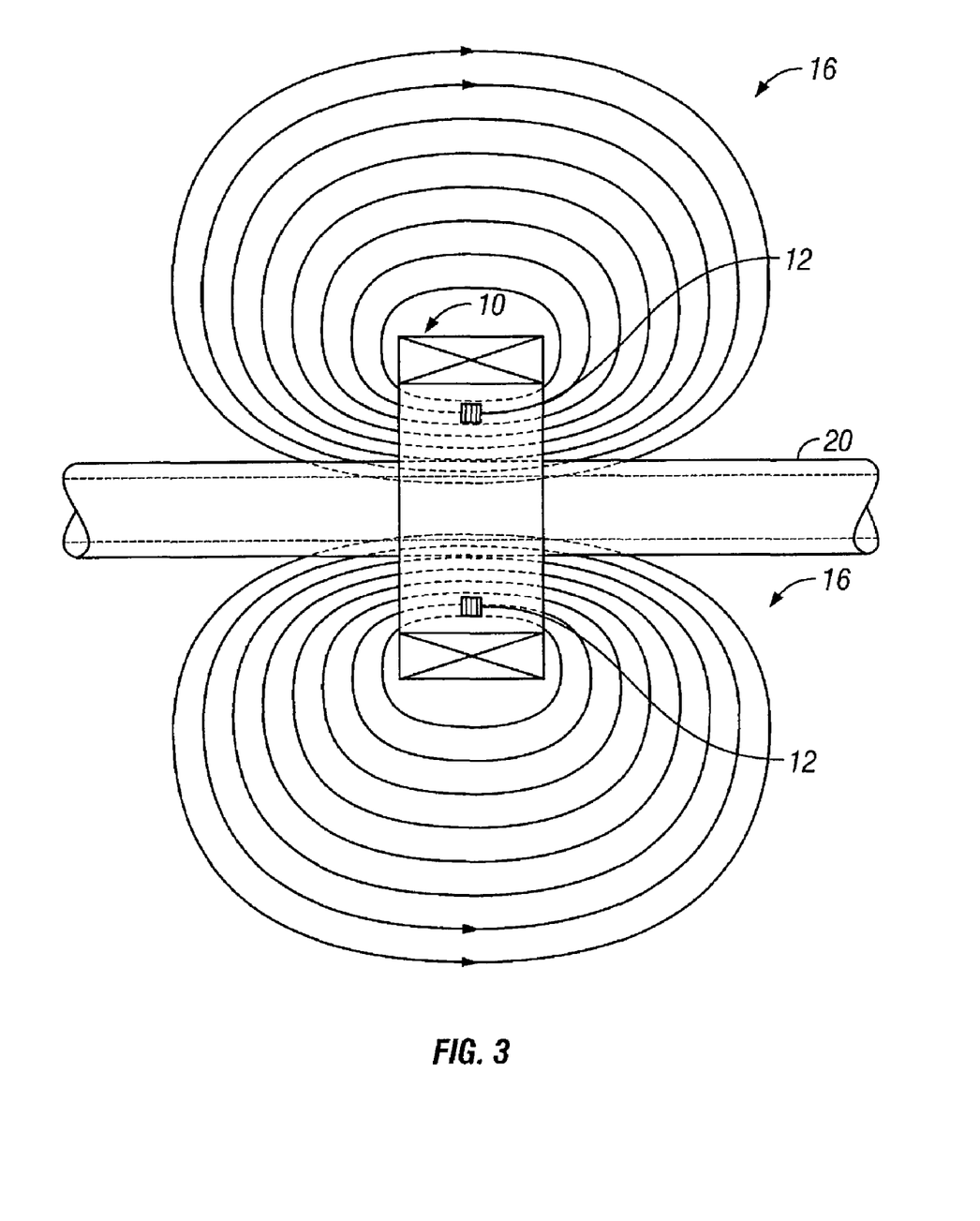
FIG. 3 schematically illustrates a side-view of the embodiment of FIGS. 1A and 1B with a pipe shown disposed through the inventive device.

Referring now to FIG. 3, a ferromagnetic object 20 (as shown a pipe) is moved through the center of the magnetic field generator. As illustrated, the magnetic flux lines 16 are drawn into the ferromagnetic material of the pipe since it offers a path of less resistance to the flux line flow 16 than does the surrounding air. When these magnetic flux lines 16 are drawn into the wall of the pipe, fewer magnetic flux lines 16 flow through the hall units 12, causing a change of voltage of the hall units 12.

Figure 4A:
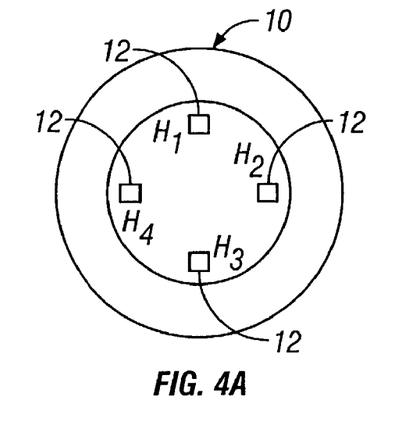
FIG. 4A schematically illustrates an end-view of an embodiment of the monitoring device.
Figure 4B:
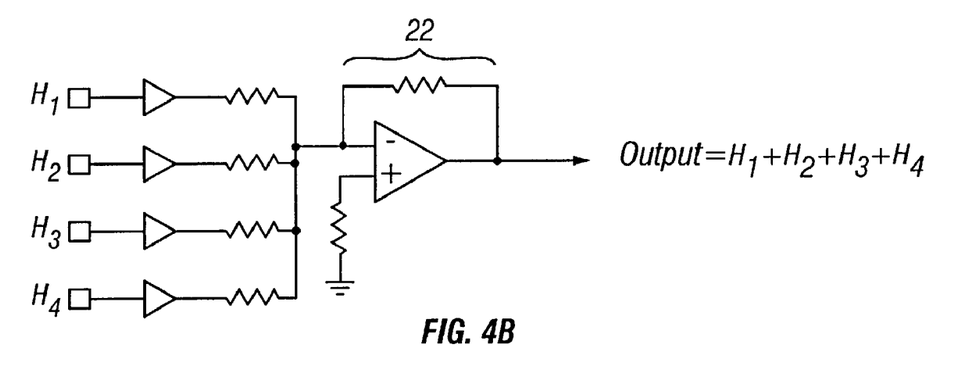
FIG. 4B schematically illustrates an electronic circuit of an embodiment of the present invention.

Referring to FIG. 4A, four hall units (H1, H2, H3 and H4) are located around the inside diameter (mounted about the inner circumference) of the magnetic field generator. Turning to FIG. 4B, a simplified schematic of an electronic circuit is illustrated where output of the four hall units (H1, H2, H3 and H4) are added together. This is accomplished by the summing amplifier 22 as shown. In other words, the voltages are generated by H1, H2, H3, and H4 are all added together such that the output is the sum of these four hall units.

One advantage of this circuit shown in FIG. 4B is that while the pipe is passed through the center of the magnetic coil, the pipe may become off center. If the pipe moves off center such that the voltage generated in H1 decreases in magnitude, the voltage generated in H3 will increase by an amount approximately equal to the decrease in H1. Therefore, the sum of the output of H1 and H3 remains more or less the same for pipe centered or off-centered. This is true regardless of what position the pipe may take off-centered in the magnetic field generator. The voltages from the four hall units will act in such a way as to null out the effect of being off-center.

Figure 5A:
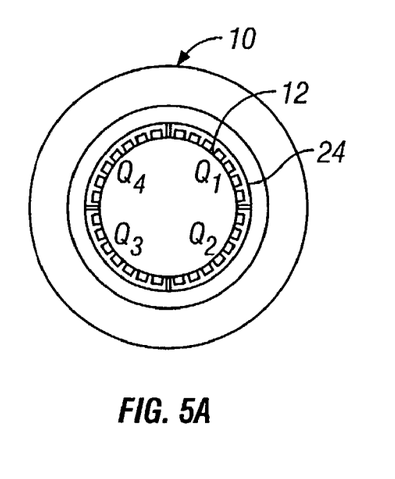
FIG. 5A schematically illustrates an end-view of an embodiment of the present invention.

Referring now to FIG. 5A, another embodiment of the present invention is illustrated. An encircling ring 24 containing a large number of hall units is illustrated. An increased number of halls units improve the sensitivity to small areas of wall loss. In the exemplified embodiment, the ring is divided into multiple quadrants, in this embodiment four quadrants (Q1, Q2, Q3 and Q4). As shown in FIG. 5A, four groups of hail unit circuitry is utilized. An increase in the number of groups will increase the sensitivity of the wall monitoring device.

Figure 5B:
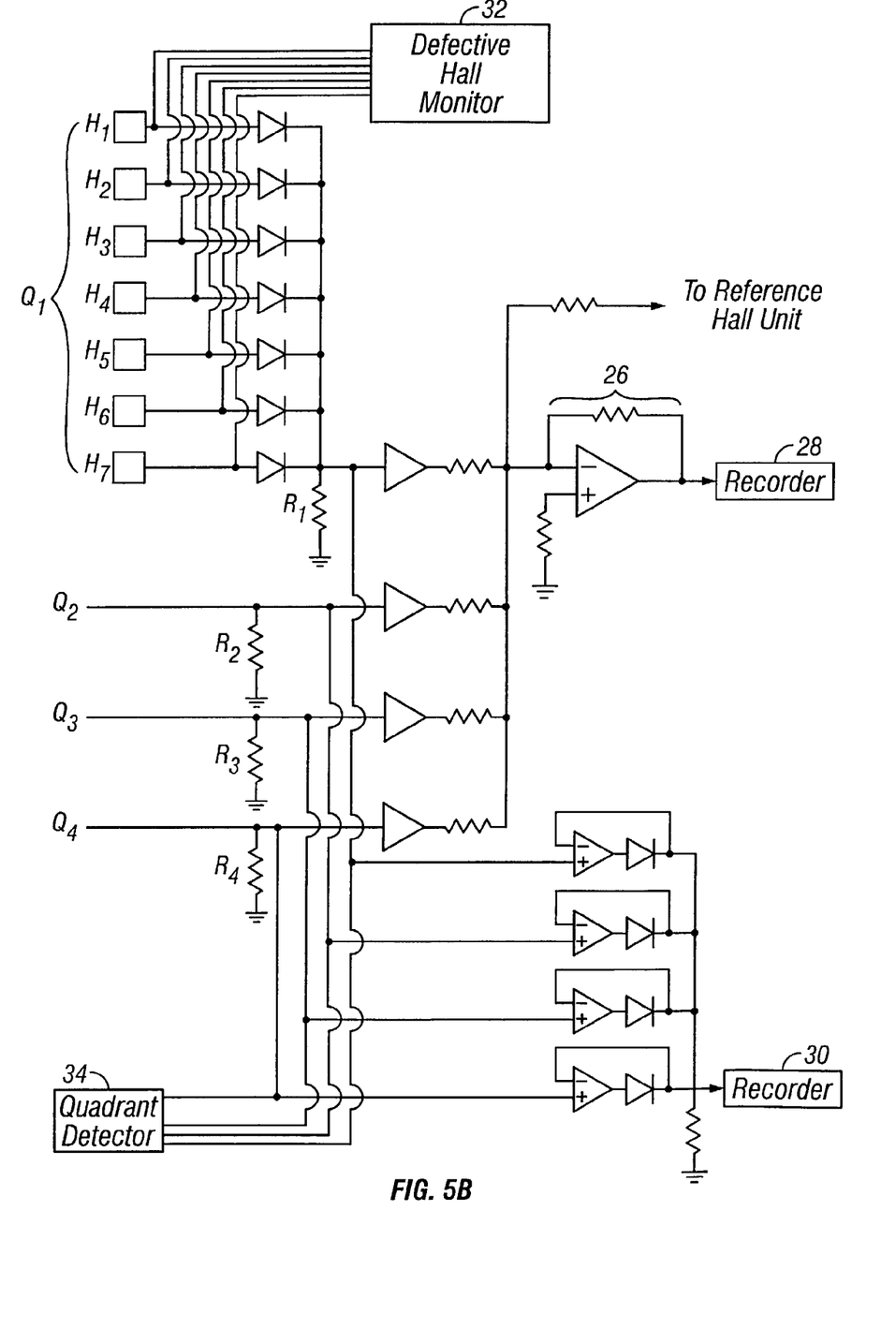
FIG. 5B schematically illustrates an electronic circuit of an embodiment of the present invention.

The circuit for one quadrant (Q1) is now described. Referring to FIG. 5B, all of the multiple hall units located in quadrant number one (Q1) have each of their outputs going to a diode and then the output of the diodes are joined together with resistor R1. The characteristic of this circuit is that the signal occurring in R1 will be from the hall unit having the largest signal. The output of R1 is fed into a summing amplifier 26 and considering the other quadrants say Q2, Q3, and Q4, they have the same diode circuit as Q1 and all of these outputs are summed together through the summing amplifier 26. The output from the summing amplifier may be displayed on a digital meter readout, a strip chart recorder or any other type of recording device 28.

Also, in this embodiment the outputs of all four quadrants (Q1, Q2, Q3 and Q4) are once ored together so that only the largest signal from each of the quadrants goes to a digital recorder, a strip chart recorder, or any other type of recording device 30 and represents the maximal signal occurring in any one of the four quadrants.

Also shown is a defective hall unit monitor to identify a defective hall monitoring circuit 32. In this case, the output off of each hall unit, before it goes to the diode, goes directly into a monitor 32. This monitor 32 detects whether or not the hall unit has failed and if it fails then a signal is outputted to the operator so he can make whatever corrective action is necessary.

Additionally shown is a defect quadrant detector 34 for warning the operator so that he is able to determine whether or not the signal that he is viewing whether it be from the summing amplifier or from the ore circuit whether that signal came from quadrant 1, 2, 3 or 4. This helps the operator to quickly identify the area to look at as far as locating a defect.

Figure 6A:
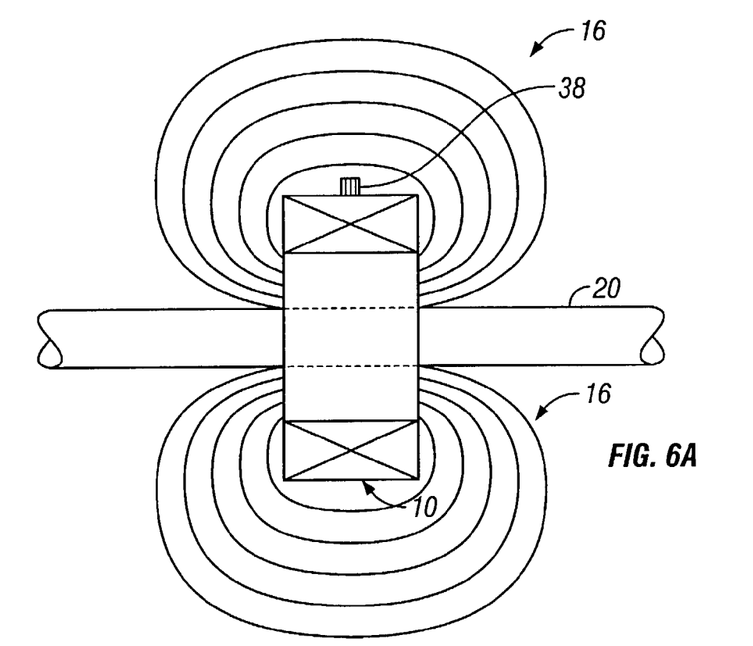
FIG. 6A schematically illustrates a side-view of an embodiment of the present invention with a pipe shown disposed through the inventive device.

Referring now to FIG. 6A, the magnetic field generator and the hall unit searching head 38 located near the center of a long piece of pipe 20 and in this particular case the flux lines encircling the coil are fairly uniform and are symmetrical. Now if we look at FIG. 6B as the end of the pipe 20 approaches the edge of the magnetizing coil and the hall's centers, the end 36 of the pipe 20 will distort the magnetic field in such a way as to cause the base line of the output of the various recorders to shift making it very difficult for the operator to interpret whatever signal maybe in this region. For compensation of this base line shift, a hall unit 38 is located on the outside periphery of the magnetic field generator. In this position, the hall unit is remote from the pipe 20 so it does not see changes in the wall of the pipe itself, but the hall unit will discern changes in the flux line pattern 16. In this particular case, when the end 36 of the pipe 20 approaches the magnetic field generator 10, this flux lines change due to the end 36 of the pipe 20 will be sent back to the summing amplifier as shown in FIG. 5 and it is called the reference input. In this particular case, the hall unit is oriented on the outside of the magnetic field generator in such a way that it's output has an opposite polarity to the other incoming signals from the quadrant detectors. Therefore, when the flux pattern changes due to the end of the pipe, it inputs a signal which compensates with this end area effect.

For wall analysis preferably the quadrants are each placed in a housing. The best results for wall analysis are obtained when the quadrants are located nearest the pipe. Various means to adjust the placement of the quadrants in close proximity to the inspected pipe may be used. For example, the quadrants may be attached to an air cylinder. For inspection of a particular pipe, the air cylinder is then actuated to maneuver the quadrant toward the outer diameter of the pipe. When set in position the air cylinder is locked in place. The pipe is then moved through the monitoring device for inspection of potential flaws.

Referring now to FIG. 6A, the magnetic field generator and the hail unit searching head 38 located near the center of a long piece of pipe 20 and in this particular case the flux lines encircling the coil are fairly uniform and are symmetrical. Now if we look at FIG. 6B as the end of the pipe 36 approaches the edge of the magnetizing coil and the hall's centers, the end 36 of the pipe 20 will distort the magnetic field in such a way as to cause the base line of the output of the various recorders to shift making it very difficult for the operator to interpret whatever signal maybe in this region.

Figure 6B:
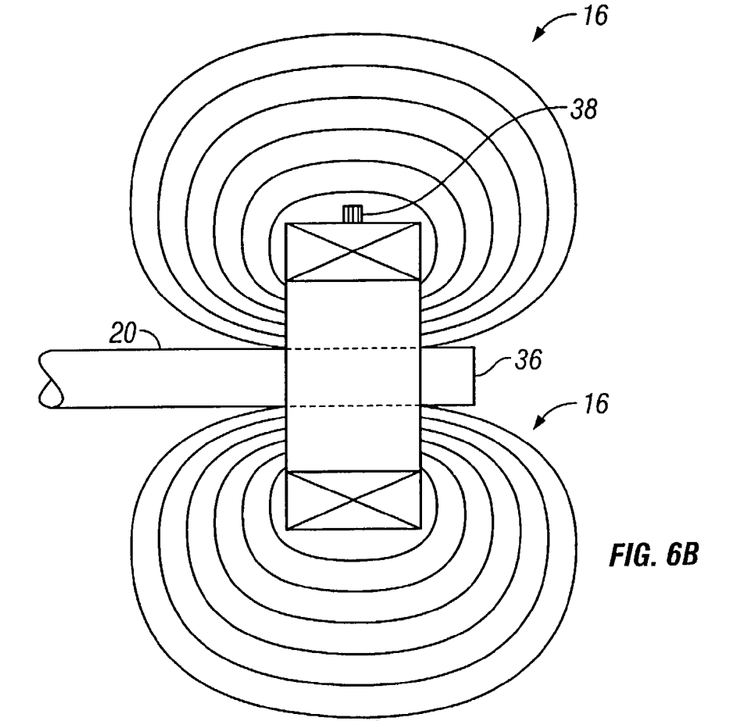
FIG. 6B schematically illustrates a side-view of an embodiment of the present invention with a pipe shown disposed through the inventive device.

For compensation of this base line shift, a hall unit 38 is located on the outside periphery of the magnetic field generator. In this position, the hail unit is remote from the pipe 20 so it does not see changes in the wall of the pipe itself, but the hall unit will discern changes in the flux line pattern 16. In this particular case, when the end 36 of the pipe 20 approaches the magnetic field generator 10, this flux lines change due to the end 36 of the pipe 20 will be sent back to the summing amplifier as shown in FIG. 5 and it is called the reference input. In this particular case, the hall unit is oriented on the outside of the magnetic field generator in such a way that it's output has an opposite polarity to the other incoming signals from the quadrant detectors. Therefore, when the flux pattern changes due to the end of the pipe, it inputs a signal which compensates with this end area effect.

Figure 7A:
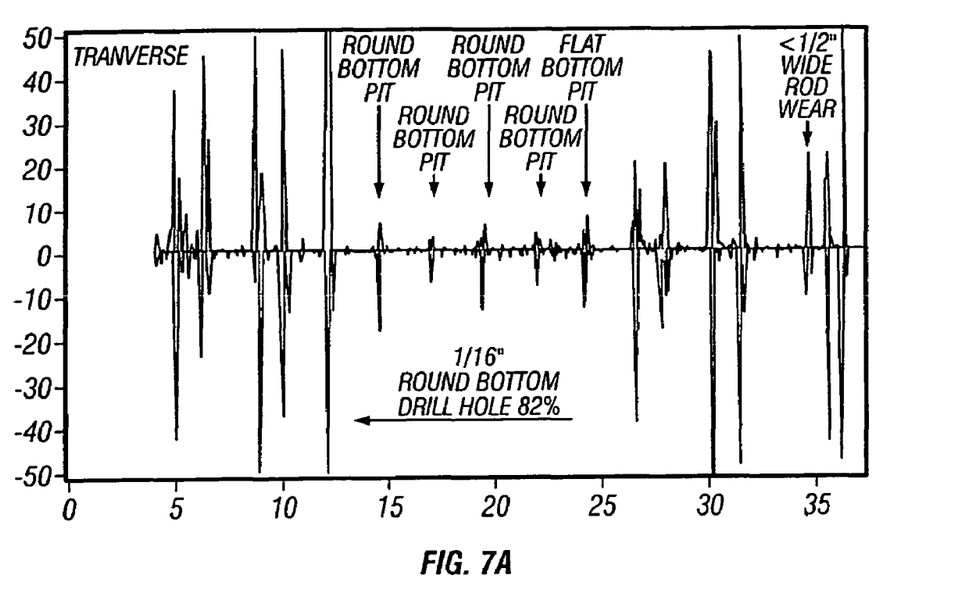
FIG. 7 graphically illustrates an inspection of a pipe with pre-fabricated defects.
Figure 7B:
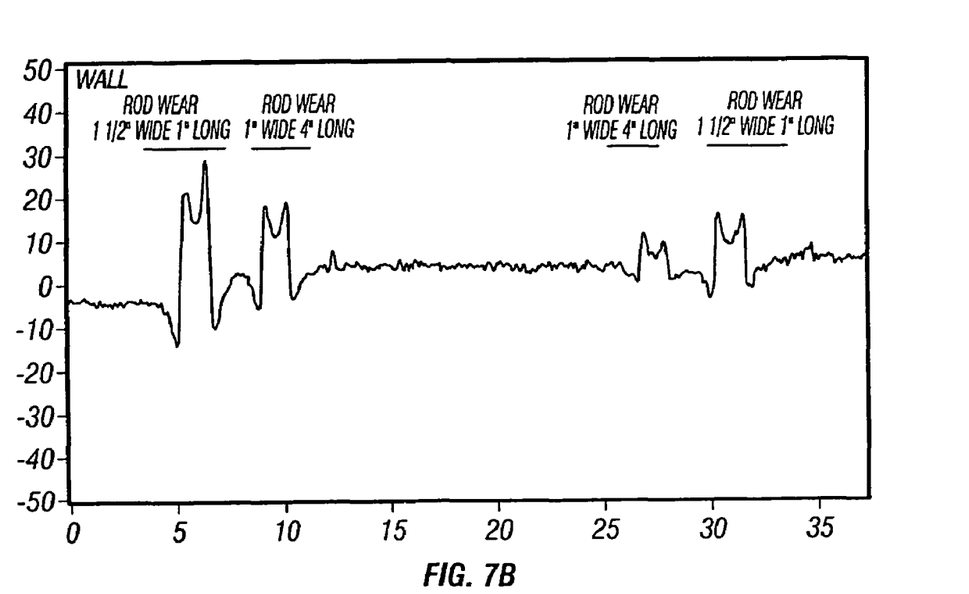

The report shown in FIG. 7 is illustrative of the results of the test. The top half of the report illustrates an inspection of pipe showing defects with transverse component. The bottom half of the report illustrates the same pipe in the top half of the report, but instead show the wall loss. In identifying transverse flaws, the monitoring device evaluates a vertical field. For example, a defect on the inner diameter would cause the flux to bridge out of the pipe and have a vertical component to it. This vertical component can determine among other flaws, crack, seams, pits, etc. In identifying wall loss, the monitoring device evaluates the horizontal component of the field, looking at the field parallel to the surface of the pipe. A change in the wall thickness will change the magnetic flux adjacent to the wall circumference.

As the pipe moved through the magnetic field, the monitoring device identified the prefabricated defects. Referring first to the Transverse defects report. Starting from right to left, as the pipe enters, the monitoring device will pick up the leading and trailing edge of the rod wear. The first defect found is inner diameter rod wear. Next an inner diameter flat bottom pit is shown. Next is an inner diameter round bottom pit. Although, both the flat bottom pit and the round bottom pit are a similar depth, the flat bottom pit is more pronounced. This is due to a greater fluctuation in the magnetic field caused by the straight walls and corners of the flat bottom pit. Whereas the round bottom pit causes a smoother fluctuation of the magnetic field due to the rounded edge of the round bottom pit. As shown on the top half of the report, other defects are shown.

The bottom half of the report illustrates wall loss of the pipe. When measuring the wall deficiency, measurement is taken for the base line. The x-axis of the report shows the footage. The y-axis of the report shows the amplitude of the signal.

The first defect shown is an inner diameter rod wear which is 1½ inches wide and 4 inches long. Next is illustrated an inner diameter rod wear which is 1 inch wide and 4 inches long. As shown on the bottom half of the report, other defects are shown. This report may be created by an analog printing device that plots the readings of the magnetic fluctuations.

Although not shown, when using an embodiment of the invention having multiple quadrants, the signal shown is the average signal. The quadrant producing the greatest voltage signal may be identified on the report. For example, if the monitoring device utilizes four quadrants, then the pipe is effectively divided into fourths for monitoring purposes. As the number of quadrants increases, the sensitivity to determining location of the wall defect can be increased. The identity of the quadrant or quadrants generating the greatest signals can be captured. These quadrants can be displayed on a report along with the defect to aid one in the physical inspection of the pipe, for example through ultra-sonic evaluation means.

The fluctuation readings in one embodiment may be printed directly to an analog plotting device. In another embodiment, the fluctuation (voltage) readings may be converted from an analog signal and translated into a digital signal. This digital signal may then be stored and utilized with a computer. The fluctuation information may then be displayed in various reports graphically on a monitor or printed to a printer or plotting device.

As discussed herein, an embodiment of the invention utilized analog circuits. The circuits, instead of being analog, may be digital such as using a computer based circuit to achieve the same result of the analog circuit. For, example the summing circuit is shown in its analog form, one skilled in the art however can take the circuit and use computer software to take the same signals and produce the same result. As such, the invention is not limited to an analog only form, but includes analog, digital, and a combination thereof.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A device for ferromagnetic wall monitoring comprising:
   a magnetic field generator for generating a magnetic field of flux, said magnetic field generator having an inner and outer circumference;
   a plurality of groups of magnetic fluctuation detectors mounted about the magnetic field generator inner circumference;
   each group of said plurality of groups of magnetic fluctuation detectors having a corresponding summing circuit interconnected therewith for separately adding together voltage outputs of all the magnetic fluctuation detectors in each group, thereby allowing determination of which group has a highest voltage output from among all of the groups; and
   a searching head adapted to detect changes in lines of the magnetic field of flux due to an end of a ferromagnetic object, the searching head mounted about the outer circumference of the magnetic field generator.

2. The device for ferromagnetic wall monitoring of claim 1, wherein the magnetic field of flux is horizontal.

3. The device for ferromagnetic wall monitoring of claim 1, wherein the magnetic field generator is an encircling coil.

4. The device for ferromagnetic wall monitoring of claim 1, wherein the magnetic field generator is a circular coil having multi-turns of wire located in the coil.

5. The device for ferromagnetic wall monitoring of claim 1, further comprising a defect monitor interconnected with each group of the magnetic fluctuation detectors.

6. The device for ferromagnetic wall monitoring of claim 1, further comprising one or more magnetic fluctuation detectors mounted about the outer circumference of the magnetic field generator.

7. The device for ferromagnetic wall monitoring of claim 6, wherein the magnetic fluctuation detectors mounted about the outer circumference are hall units.

8. The device for ferromagnetic wall monitoring of claim 6, the magnetic fluctuation detectors mounted about the outer circumference are magneto resistors.

9. The device for ferromagnetic wall monitoring of claim 6, the magnetic fluctuation detectors mounted about the outer circumference are magneto diodes.

10. The device for ferromagnetic wall monitoring of claim 6, wherein the magnetic field fluctuation detectors mounted about the outer circumference are selected from hall units, magneto resistors, magneto diodes and combinations thereof.

11. The device for ferromagnetic wall monitoring of claim 1, further comprising an ore circuit interconnected with each magnetic fluctuation detector in each of said groups whereby a largest signal occurring in each of the groups is determined.

12. A device for ferromagnetic wall monitoring comprising:
    a circular coil having multi-turns of wire located in the coil for generating a horizontal magnetic field of flux, said circular coil having an inner and outer circumference;
    a plurality of groups of hall units mounted about the circular coil inner circumference;
    each group of said plurality of groups of hail units having a corresponding summing circuit interconnected therewith for separately adding together voltage outputs of all the hall units in each group, thereby allowing determination of which group has a highest voltage output from among all of the groups; and
    a searching head adapted to detect changes in lines of the magnetic field of flux due to an end of a ferromagnetic object, the searching head mounted about the outer circumference of the magnetic field generator.

13. The device for ferromagnetic wall monitoring of claim 12, wherein said hall units within a group are mounted substantially equidistant from one another.

14. The device for ferromagnetic wall monitoring of claim 12, further comprising an ore circuit interconnected with each hall unit in each of said groups whereby a largest signal occurring in each of the groups is determined.

15. The device for ferromagnetic wall monitoring of claim 12, further comprising a defect monitor interconnected with each group of hall units.

16. A method for ferromagnetic wall monitoring, comprising the steps of:
    providing a magnetic field generator having a plurality of groups of magnetic field fluctuation detectors mounted about the inner circumference of the magnetic field generator, and a searching head able to detect magnetic field fluctuations due to an end of a ferromagnetic object, the searching head mounted about an outer circumference of the magnetic field generator;
    generating a magnetic field of flux with said magnetic field generator;
    passing the ferromagnetic object through said magnetic field of flux;
    separately adding together voltage outputs of all magnetic field fluctuation detectors in each of the groups thereby determining which group has a highest voltage output of the groups;
    determining wall thickness of and/or flaws in said ferromagnetic object by identifying magnetic field fluctuations with said plurality of magnetic field fluctuation detectors; and
    determining the end of said ferromagnetic object by detecting magnetic field fluctuations with said searching head.

17. The method of claim 16, wherein the magnetic field fluctuation detectors are magneto resistors.

18. The method of claim 16, wherein the magnetic field fluctuation detectors are magneto diodes.

19. The method of claim 16, wherein the ferromagnetic object is a pipe.

20. The method of claim 16, wherein the magnetic field fluctuation detectors are hall units.

21. The method of claim 20, determining a sum of voltage from each of said hall units.

22. The method of claim 20, further comprising the step of monitoring a signal generated by said hail units when said ferromagnetic object passes near said hall units.

23. The method of claim 16, wherein the magnetic field generator is an encircling coil.

24. The method of claim 16, wherein the magnetic field generator is a circular coil having multi-turns of wire located in the coil.

25. The method of claim 16, wherein the magnetic field fluctuation detectors are selected from hall units, magneto resistors, magneto diodes and combinations thereof.

26. The method of claim 16, further comprising exciting the magnetic field generator with a DC current for generating magnetic flux that encircle the magnetic field generator.

27. The method of claim 20, further comprising detecting a change of voltage in said hall units when passing a portion of pipe past hall units, indicating said portion of pipe having a flaw.

28. The method of claim 20, further comprising identifying the greatest voltage signal from a group of magnetic field fluctuation detectors.

29. A device for ferromagnetic wall monitoring comprising:
    a magnetic field generator for generating a magnetic field of flux, said magnetic field generator having an inner and outer circumference;
    a plurality of groups of magnetic fluctuation detectors mounted about the magnetic field generator inner circumference;
    each group of said plurality of groups of magnetic fluctuation detectors having a corresponding summing circuit interconnected therewith for separately adding together voltage outputs of all the magnetic fluctuation detectors in each group, thereby allowing determination of which group has a highest voltage output from among all of the groups;
    a searching head adapted to detect changes in lines of the magnetic field of flux due to an end of a ferromagnetic object; and
    an ore circuit interconnected with each magnetic fluctuation detector in each of said groups whereby a largest signal occurring in each of the groups is determined.

30. A device for ferromagnetic wall monitoring comprising:

a circular coil having multi-turns of wire located in the coil for generating a horizontal magnetic field of flux, said circular coil having an inner and outer circumference;

a plurality of groups of hall units mounted about the circular coil inner circumference;

each group of said plurality of groups of hall units having a corresponding summing circuit interconnected therewith for separately adding together voltage outputs of all the hail units in each group, thereby allowing determination of which group has a highest voltage output from among all of the groups;

a searching head mounted adapted to detect changes in lines of the magnetic field of flux due to an end of a ferromagnetic object; and an ore circuit interconnected with each magnetic fluctuation detector in each of said groups whereby a largest signal occurring in each of the groups is determined.

31. A method for ferromagnetic wall monitoring, comprising the steps of:

providing a magnetic field generator having a plurality of groups of magnetic field fluctuation detectors mounted about an inner circumference of the magnetic field generator, and a searching head mounted in a position to detect magnetic field fluctuations due to an end of a ferromagnetic object;

generating a magnetic field of flux with said magnetic field generator;

passing the ferromagnetic object through said magnetic field of flux;

separately adding together voltage outputs of all magnetic field fluctuation detectors in each of the groups thereby determining which group has a highest voltage output of the groups;

determining wall thickness of and/or flaws in said ferromagnetic object by identifying magnetic field fluctuations with said plurality of magnetic field fluctuation detectors; and determining the end of said ferromagnetic object by detecting magnetic field fluctuations with said searching head;

determining a largest signal occurring in each of the groups using an ore circuit interconnected with each magnetic fluctuation detector in each of said groups.

* * * * *